United States Patent [19]

Stahl et al.

[11] Patent Number: 4,639,338

[45] Date of Patent: Jan. 27, 1987

[54] PREPARATION OF CRYSTALLINE DISODIUM 3-AMINO-1-HYDROXYPROPANE-1,1-DIPHOSPHONATE PENTAHYDRATE

[75] Inventors: Peter H. Stahl, Freiburg i/Br., Fed. Rep. of Germany; Beat Schmitz, Allschwil, Switzerland

[73] Assignees: Ciba-Geigy Corporation, Ardsley, N.Y.; Henkel Kommanditgesellschaft auf Aktien, Düsseldorf-Holthausen, Fed. Rep. of Germany

[21] Appl. No.: 759,985

[22] Filed: Jul. 29, 1985

[30] Foreign Application Priority Data

Aug. 6, 1984 [CH] Switzerland .................... 3768/84

[51] Int. Cl.⁴ .................... C07F 9/38; A61K 31/045; A61K 31/66
[52] U.S. Cl. .................... 260/502.5 C
[58] Field of Search .................... 260/502.5 C

[56] References Cited

U.S. PATENT DOCUMENTS

| | | |
|---|---|---|
| 3,962,432 | 6/1976 | Schmidt-Dunker ................ 514/129 |
| 4,054,598 | 10/1977 | Blum et al. .................... 260/502.5 C |
| 4,086,334 | 4/1978 | Schmidt-Dunker et al. ........ 514/11 |
| 4,134,969 | 1/1979 | Schmidt-Dunker ................ 514/108 |
| 4,304,734 | 12/1981 | Jary et al. .................... 260/502.5 C |
| 4,327,039 | 4/1982 | Blum et al. .................... 260/502.5 C |
| 4,407,761 | 10/1983 | Blum et al. .................... 260/502.5 C |
| 4,446,052 | 5/1984 | Sunberg et al. ............... 260/502.5 C |

FOREIGN PATENT DOCUMENTS 2130794 11/1973 Fed. Rep. of Germany .

OTHER PUBLICATIONS

Chem. Abstr. 78, 94528z.

*Primary Examiner*—J. E. Evans
*Attorney, Agent, or Firm*—Michael W. Glynn; Irving M. Fishman

[57] ABSTRACT

The invention relates to a novel crystal modification, containing water of crystallization, of disodium 3-amino-1-hydroxypropane-1,1-diphosphonate of the formula

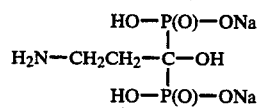

and to a process for the manufacture thereof. This modification is suitable for the oral treatment of disorders of the calcium and phosphate metabolism and associated diseases in warm-blooded animals.

11 Claims, No Drawings

PREPARATION OF CRYSTALLINE DISODIUM 3-AMINO-1-HYDROXYPROPANE-1,1-DIPHOSPHONATE PENTAHYDRATE

The invention relates to a novel crystal modification, containing water of crystallisation, of disodium 3-amino-1-hydroxypropane-1,1-diphosphonate of the formula

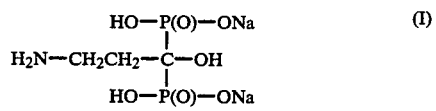

and a process for the manufacture thereof.

The 3-amino-1-hydroxypropane-1,1-diphosphonic acid on which the disodium salt of the formula I is based, a process for its manufacture and its use as a complex-forming component of washing agents are described in German Auslegeschrift No. 2,130,794. According to German Offenlegungsschrift No. 2,405,254, the mentioned acid and its water-soluble salts are also suitable as the active ingredients of medicaments for treating disorders of the calcium and phosphate metabolism and associated diseases in warm-blooded animals. In particular, according to German Offenlegungsschrift No. 2,553,963, it is possible by means of the simultaneous oral administration of 3-amino-1-hydroxypropane-1,1-diphosphonic acid or of a water-soluble salt thereof, especially disodium 3-amino-1-hydroxypropane-1,1-diphosphonate (I), to reduce the dose of calcitonin required for a specific therapeutic effect in comparison with the dose required for calcitonin monotherapy.

Although disodium 3-amino-1-hydroxypropane-1,1-diphosphonate (I) and its usefulness as an active ingredient of medicaments may thus be considered to be known in the prior art, the publications mentioned contain no precise instructions for its manufacture. For example, all that can be found in German Offenlegungsschrift No. 2,553,963 is that 3-amino-1-hydroxypropane-1,1-diphosphonic acid can "be converted into the desired salts by means of complete or partial neutralisation".

According to the customary neutralisation process, however, disodium 3-amino-1-hydroxypropane-1,1-diphosphonate is obtained in hygroscopic form and with unsatisfactory crystallinity. If the neutralisation is carried out, for example, using the method described in Example 2 of U.S. Pat. No. 4,304,734 for the manufacture of the homologous disodium 6-amino-1-hydroxyhexane-1,1-diphosphonate (Comparison Example 1), an amorphous product is obtained which, even after drying at approximately 60° under reduced pressure until the weight is constant, still has hygroscopic properties, that is to say takes up varying amounts of water as a function of the ambient humidity. This makes it much more difficult to process into a form of pharmaceutical administration suitable for enteral, such as oral, administration and reduces the storage stability of such forms of administration to an unacceptable degree.

The first attempts to obtain a defined crystalline form of disodium 3-amino-1-hydroxypropane-1,1-diphosphonate that is stable to storage under approximately normal ambient conditions by modifying the neutralisation or working-up conditions, and thus to avoid the difficulties indicated, were not successful. It was found that, depending on the method used, a plurality of different solid forms were produced that could be differentiated by their X-ray powder patterns and their IR spectra. If, for example, an aqueous solution of disodium 3-amino-1-hydroxypropane-1,1-diphosphonate is extensively concentrated at approximately 75° C., the product is allowed to crystallise out by means of slow cooling in a temperature range of from approximately 45° C. to approximately 0° C., and is then filtered with suction and dried at room temperature under reduced pressure until the weight is constant (Comparison Example 2), disodium 3-amino-1-hydroxypropane-1,1-diphosphonate is obtained in a crystal form designated according to the characteristics of its X-ray powder pattern "modification B". If an analogous method is used, but the drying is carried out at approximately 120° C. (Comparison Example 3), a further crystal form, this time substantially anhydrous, designated as "modification A" is obtained. If an analogous method is again used, but ethanol is added after the concentration at approximately 70°-80° C., and the whole is allowed to crystallise while cooling and dried at approximately 120° C. under reduced pressure until the weight is constant (Example 5, starting material), "modification C", which is only moderately crystalline, is obtained. None of these modifications had the storage stability required of an active ingredient in an enterally, such as orally, administrable medicament. Furthermore, none of the methods mentioned could be reproduced on at least a semi-industrial scale.

There was therefore a need for the surprising discovery that disodium 3-amino-1-hydroxypropane-1,1-diphosphonate is obtained in a crystal modification, designated hereinbelow "modification E", that is stable to storage and contains water of crystallisation, if the crystal formation is initiated at at least 50° C. and drying is carried out at normal or slightly elevated temperature, or if solid forms of disodium 3-amino-1-hydroxypropane-1,1-diphosphonate that contain relatively little water are treated with water.

The novel crystal modification, containing water of crystallisation, of disodium 3-amino-1-hydroxypropane-1,1-diphosphonate (modification E) has a characteristic X-ray powder pattern which can be clearly differentiated from those of modifications A, B and C and can be used to characterise the novel modification E. Its mode of manufacture can, however, also be used for characterisation.

Modification E of disodium 3-amino-1-hydroxypropane-1,1-diphosphonate contains from approximately 24.1 to approximately 24.5% by weight, that is to say per mol thereof approximately 5 mol, of water. It is therefore assumed that, according to crystal chemistry, it is a pentahydrate.

It has excellent crystallinity and is completely stable to storage under approximately normal ambient conditions. For example, it has been found that neither changing the relative atmospheric humidity in a range of from approximately 10 to approximately 95%, nor heating to approximately 60° C., even under quasiisothermal conditions, nor storing for 3 months at approximately from 40° to 60° C. and at approximately from 30 to 55% relative atmospheric humidity, nor storing for 3 weeks at room temperature and at approximately 92% relative atmospheric humidity brings about a detectable change in the X-ray powder pattern or the IR spectrum.

Modification E of disodium 3-amino-1-hydroxypropane-1,1-diphosphonate according to the invention can therefore be processed without difficulty to form enterally, such as orally, administrable medicinal preparations that are stable to storage. The provision of this modification thus makes it practicable for the first time to make available medicinal preparations of disodium 3-amino-1-hydroxypropane-1,1-diphosphonate intended for enteral, such as oral, administration.

The invention accordingly relates also to a novel process for the manufacture of the novel crystal modification, containing water of crystallisation, of disodium 3-amino-1-hydroxypropane-1,1-diphosphonate. This process is characterised in that disodium 3-amino-1-hydroxypropane-1,1-diphosphonate is caused to crystallise from a water-containing solution or that a solid form of disodium 3-amino-1-hydroxypropane-1,1-diphosphonate that contains relatively little water is treated with water, and in each case the product is isolated and dried at normal or slightly elevated temperature.

A water-containing solution of disodium 3-amino-1-hydroxypropane-1,1-diphosphonate is to be understood as meaning, for example, a solution of disodium 3-amino-1-hydroxypropane-1,1-diphosphonate in water or a mixture of water and a water-miscible organic solvent or diluent. As solvent or diluent there come into consideration especially lower alkanols, that is to say alkanols having from 1 to 7, especially from 1 to 4, carbon atoms, especially ethanol or, secondly, methanol. Preferred are aqueous or aqueous/ethanolic solutions having an ethanol content of not more than 40% by volume.

Solid forms of disodium 3-amino-1-hydroxypropane-1,1-diphosphonate that contain relatively little water are, for example, crystalline solid forms thereof having a content of water of crystallisation of less than approximately 24% by weight, especially substantially anhydrous disodium 3-amino-1-hydroxypropane-1,1-diphosphonate (modification A) and modification C thereof, which contains water of crystallisation.

The crystallisation of disodium 3-amino-1-hydroxypropane-1,1-diphosphonate from a water-containing solution is effected in customary manner from an at least saturated solution, it being possible to differentiate between a crystal-formation phase and a crystal-growth phase.

Crystal formation may occur spontaneously, for example on solid particles suspended in the solution or at the surface of the reaction vessel or stirring apparatus but is advantageously initiated by inoculation, that is to say the introduction of seed crystals. If no seed crystals are available, they can be manufactured in customary manner, advantageously in an aliquot portion of the solution, for example by means of vigorous shaking, the introduction of powdered glass, scratches on the vessel wall or super-cooling. It is, however, also possible to supercool the whole solution slightly, that is to say by a few degrees, for example from 2° to 5° C., in order to promote spontaneous crystal formation, and then to heat it to the starting temperature again.

Crystal growth is effected especially by lowering the saturation concentration, for example by cooling or by adding a diluent in which disodium 3-amino-1-hydroxypropane-1,1-diphosphonate is less soluble than it is in water, such as one of the mentioned water-miscible diluents, or by combining the two and optionally using suitable additional measures. During this process, the rate of cooling and/or the rate of supply of the diluent should be so matched to the rate of growth of the crystals that significant supersaturation of the solution is avoided.

The novel crystal modification, containing water of crystallisation, that is formed can be isolated from its water-containing suspension with the aid of any available method of separating binary solid/liquid systems, for example by filtration, pressure filtration (filtration with suction), centrifugation or decanting. In order to remove impurities in remaining mother liquor residues, the residues can be washed with water or preferably with an aqueous alkanol having from 1 to 7, especially from 1 to 4, carbon atoms, for example with approximately from 40 to 60% ethanol or 50 to 75% methanol.

Drying is effected at normal or slightly elevated temperature, for example in a temperature range of from approximately 15° to approximately 60° C., preferably at from approximately 18° to approximately 25° C. (room temperature) or at from approximately 35° to approximately 40° C., and is continued until the weight is approximately constant. In order to accelerate drying, the operation can be carried out under reduced pressure, a so-called water-jet vacuum (from approximately 5 to approximately 25 mbar) being quite adequate.

The manufacture of at least saturated solutions of disodium 3-amino-1-hydroxypropane-1,1-diphosphonate is effected in customary manner, for example by dissolving a solid form thereof in a water-containing medium or, advantageously in situ, by partially neutralising 3-amino-1-hydroxypropane-1,1-diphosphonic acid with a basic sodium salt in a water-containing medium and, if necessary, converting an initially unsaturated solution of disodium 3-amino-1-hydroxypropane-1,1-diphosphonate into a saturated solution.

Basic sodium salts suitable for the partial neutralisation of 3-amino-1-hydroxypropane-1,1-diphosphonic acid are, for example, sodium hydroxide or sodium carbonate.

Preferably 3-amino-1-hydroxypropane-1,1-diphosphonic acid in an aqueous suspension is reacted with at least that amount of aqueous sodium hydroxide solution that is required for the formation of disodium 3-amino-1-hydroxypropane-1,1-diphosphonate, that is to say aqueous sodium hydroxide solution, preferably approximately 30 to 40% strength, is added to an aqueous suspension of 3-amino-1-hydroxypropane-1,1-diphosphonic acid until the pH value of the reaction mixture is at least 7, preferably approximately from 7.2 to 7.5.

The conversion of an unsaturated, preferably aqueous, solution of disodium 3-amino-1-hydroxypropane-1,1-diphosphonate into a saturated solution is effected in customary manner, for example by concentrating, that is to say evaporating off excess solvent, preferably water, by adding a water-miscible diluent in which disodium 3-amino-1-hydroxypropane-1,1-diphosphonate is less soluble than it is in water or, indirectly, by lowering the saturation concentration of disodium 3-amino-1-hydroxypropane-1,1-diphosphonate, for example by cooling or, secondly, by means of an additive having a like ion, such as separating by the addition of a salt.

The saturation concentration of disodium 3-amino-1-hydroxypropane-1,1-diphosphonate in a water-containing solution is greatly dependent on temperature. This allows the crystallisation to be controlled, by means of a suitable choice of starting temperature, in such a manner that the crystal growth takes place predominantly in an easily controlled temperature range of from approximately 0° to approximately 50° C. Crystal formation is, accordingly, preferably initiated at at least 50° C., preferably at from approximately 50° to approximately 80° C., especially at approximately from 55° to 70° C. This ensures that at approximately from 0° to 5° C. at least 95% of the dissolved disodium 3-amino-1-hydroxyoropane-1,1-diphosphonate crystallises out in the form of the crystal modification containing water of crystallisation according to the invention (modification E). If the crystal formation is initiated at below approximately 50° C., for example at 45° C., modification B may be formed; this can, however, be converted into modification A by heating, and modification A can in turn be converted into modification E according to the invention by treatment with water.

In a preferred embodiment of the crystallisation process described above, for example an approximately 10 to 55%, preferably approximately 12 to 28%, aqueous solution of disodium 3-amino-1-hydroxypropane-1,1-diphosphonate is concentrated at from approximately 70° to approximately 80° C., for example at approximately 75° C., to the saturation concentration of disodium 3-amino-1-hydroxypropane-1,1-diphosphonate, crystal formation is initiated, the whole is cooled slowly to approximately from 0° to 5° C. and the isolated product is dried at from approximately 20° to approximately 40° C., preferably at from approximately 35° to approximately 40° C., until the weight is approximately constant. In a different, especially preferred embodiment, an approximately 35 to 45%, for example approximately 40%, aqueous solution that has been heated to approximately from 70° to 80° C. is cooled slowly to not less than 55° C. until crystal formation starts, and is then cooled slowly, for example in the course of approximately 2 hours, in the first instance to approximately from 20° to 25° C., and then approximately 35 to 45%, for example approximately 40%, by volume (based on the total amount of water) of ethanol are added, and the whole is then further cooled slowly, for example over the course of one hour, to from 0° to approximately 5° C. and stirred for some time, for example approximately one hour, at this temperature, and the isolated product is dried at from approximately 20° to approximately 40° C., preferably from approximately 35° C. to approximately 40° C., until the weight is approximately constant.

The heat of neutralisation released during the neutralisation of 3-amino-1-hydroxypropane-1,1-diphosphonic acid can advantageously be used to provide at least part of the energy required for reaching the crystal-formation temperature.

The invention thus also relates to a process for the manufacture of disodium 3-amino-1-hydroxypropane-1,1-diphosphonate in the form of the novel modification E that contains water of crystallisation, by reacting 3-amino-1-hydroxypropane-1,1-diphosphonic acid with a basic sodium salt suitable for the partial neutralisation thereof. This process is characterised in that 3-amino-1-hydroxypropane-1,1-diphosphonic acid in a water-containing suspension and/or solution is reacted with the requisite amount of aqueous sodium hydroxide solution, the resulting disodium 3-amino-1-hydroxypropane-1,1-diphosphonate is caused to crystallise from an at least saturated water-containing solution in the form of the novel crystal form containing water of crystallisation, and the product is isolated and dried at normal or slightly elevated temperature.

The reaction conditions are advantageously so selected that the neutralisation takes place in a temperature range of from approximately 35° to approximately 85° C., preferably from approximately 35° to approximately 55° C. or from approximately 50° to approximately 85° C., the crystal formation takes place at at least approximately 50° C., for example at from approximately 50° to approximately 75° C., preferably at from approximately 50° to approximately 55° C., or at from approximately 55° to approximately 70° C., and the crystal growth occurs predominantly in a temperature range of from approximately 50° to approximately 0° C.

In a preferred embodiment of this method which combines the crystallisation of disodium 3-amino-1-hydroxypropane-1,1-diphosphonate in the novel crystal modification containing water of crystallisation from an at least saturated water-containing solution and the in situ manufacture of such a solution, for example 10 parts by weight of 3-amino-1-hydroxypropane-1,1-diphosphonic acid, suspended in approximately from 18 to 23, for example approximately 20, parts by volume of water, are neutralised at from approximately 65° to approximately 85° C. by adding that amount of from approximately 27.5 to approximately 32.5% aqueous sodium hydroxide solution necessary for the formation of disodium 3-amino-1-hydroxypropane-1,1-diphosphonate, for example approximately from 8.5 to 8.7 parts by volume, that is to say approximately 8.6 parts by volume (approximately 11.4 parts by weight) of approximately 30% aqueous sodium hydroxide solution, the resulting solution is filtered if necessary, the filtrate is washed with approximately from 1.2 to 1.6, for example approximately 1.4, parts by volume of water and the whole is allowed to cool at least to saturation, for example to from approximately 70° to approximately 55° C., then inoculated and cooled slowly, for example in the course of approximately 2 hours, to from approximately 20° to approximately 25° C., then approximately 7 to 12, for example approximately 10, parts by volume of ethanol are added and the whole is cooled slowly, for example in the course of one hour, to from approximately 0° to approximately 5° C. and then stirred at this temperature for some time, for example approximately from 1 to 15 hours, filtered with suction or centrifuged, washed in portions with a total of approximately from 7.5 to 12.5, for example approximately 10, parts by volume of approximately 40 to 60%, for example approximately 50%, aqueous ethanol and dried at slightly elevated temperature, for example at from approximately 30° to approximately 60° C., preferably at approximately from 35° to 40°, advantageously under reduced pressure, until the weight is constant.

In another preferred embodiment, for example 10 parts by weight of 3-amino-1-hydroxypropane-1,1-diphosphonic acid are suspended in from approximately 25 to approximately 35, for example approximately 32.5, parts by volume of water and heated to approximately 35° C., and there is then added that amount of approximately from 27.5 to 32% aqueous sodium hydroxide solution necessary for the formation of disodium 3-amino-1-hydroxypropane-1,1-diphosphonate, for example approximately from 8.5 to 8.7 parts by volume, that is to say approximately 8.6 parts by volume (approximately 11.4 parts by weight) of approximately 30% aqueous sodium hydroxide solution, at such a rate that the temperature rises to approximately from 52° to 58° C., for example to approximately 54° C., crystallisation is initiated approximately at this temperature and the whole is allowed to cool slowly to room temperature while stirring, then filtered with suction and washed in portions with a total of approximately from 15 to 25, for example approximately 18, parts by volume of approximately 50 to 75%, for example approximately 66%, aqueous methanol, and dried as indicated above.

The treatment with water of solid forms of disodium 3-amino-1-hydroxypropane-1,1-diphosphonate that contain relatively little water in comparison with modification E according to the invention is effected in customary manner by the action of at least that amount of water necessary for the formation of the novel form containing water of crystallisation. The water can be in a liquid or gaseous state.

In the case of the treatment with water in a liquid state, the maximum amount of water that can be used is limited by the solubility of disodium 3-amino-1-hydroxypropane-1,1-diphosphonate; it must not reach the threshold value required for complete dissolution, that is to say the multiple given by the reciprocal value, reduced by 1, of the saturation concentration of disodium 3-amino-1-hydroxypropane-1,1-diphosphonate. On the other hand, starting from substantially anhydrous disodium 3-amino-1-hydroxypropane-1,1-diphosphonate, at least approximately 32% by weight of water is required. Approximately from 2 to 3 times, for example 2.5 times, the amount by weight of water has proved ideal. The temperature at which the treatment with water in the liquid state is carried out is not critical per se. In order to minimise the losses due to the rapid increase in solubility with temperature, it is recommended, however, that the operation be carried out at normal or, especially towards the end of the treatment, slightly reduced temperature, for example at from approximately 15° to approximately 30° C., especially from approximately 20° to approximately 25° C., and towards the end, at approximately from 0° to 5° C.

In the case of the treatment with water in the vaporous state, the starting material is exposed to a water vapour-containing atmosphere, for example moist air. The duration of exposure required for conversion decreases as the relative atmospheric humidity increases. The humidity should therefore not fall substantially below approximately 90% and, in view of the possible condensation of water on the crystal surface, should be somewhat less than 100%. At from approximately 20° to approximately 25° C., moist air having a relative atmospheric humidity of from approximately 95% to approximately 99%, for example of approximately 97%, has proved very suitable.

In a preferred embodiment of this process variant moist air having a relative atmospheric humidity of approximately from 90 to 99%, for example from approximately 95% to approximately 99%, is allowed to act, for example, on substantially anhydrous disodium 3-amino-1-hydroxypropane-1,1-diphosphonate or on a different crystalline form thereof that contains less water, for example modification C, at from approximately 20° to approximately 25° C., until at least the required amount of water, that is to say at least approximately 32.2% by weight, for example from approximately 32.2 to approximately 37.5% by weight, (taking into account the initial water content) has been absorbed and the atmospheric humidity is then reduced to normal ambient values again, that is to say to from approximately 35% to approximately 80%, for example to from approximately 40% to approximately 60%.

The manufacture of solid forms of disodium 3-amino-1-hydroxypropane-1,1-diphosphonate that contain relatively little water and are used as starting material is effected by the partial neutralisation of 3-amino-1-hydroxypropane-1,1-diphosphonic acid with sodium hydroxide or sodium carbonate, crystallisation of the resulting disodium 3-amino-1-hydroxypropane-1,1-diphosphonate from an at least saturated water-containing solution, and isolation thereof as described above and suitable after-treatment. This comprises high-temperature drying by heating to from approximately 100° to approximately 160° C., for example to from approximately 120° to approximately 150° C.

For example, substantially anhydrous disodium 3-amino-1-hydroxypropane-1,1-diphosphonate (modification A) is obtained, for example, by adding to a suspension of 10 parts by weight of 3-amino-1-hydroxypropane-1,1-diphosphonic acid in approximately from 25 to 37.5, for example approximately 32, parts by volume of water that amount of approximately from 25 to 45% aqueous sodium hydroxide solution necessary for the formation of disodium 3-amino-1-hydroxypropane-1,1-diphosphonate, for example approximately from 8.4 to 8.5 parts by weight, that is to say approximately 8.5 parts by weight of approximately 40% aqueous sodium hydroxide solution, at such a rate that the reaction temperature rises to approximately from 50° to 55° C., the crystal formation is initiated at approximately from 45° to 52° C. and the whole is cooled slowly to room temperature, filtered with suction, washed in portions with a total of approximately from 10 to 20, for example approximately 16, parts by volume of approximately from 50 to 75%, for example approximately 66%, aqueous methanol and dried under reduced pressure at from approximately 120 to approximately 150° C. until the weight is constant.

In order to manufacture the crystalline modification C of disodium 3-amino-1-hydroxypropane-1,1-diphosphonate which can be used as starting material, for example a suspension of 10 parts by weight of 3-amino-1-hydroxypropane-1,1-diphosphonic acid in approximately from 70 to 100, for example approximately 92, parts by weight of water is heated to approximately 60° C., and there is then added that amount of approximately from 27.5 to 32.5% aqueous sodium hydroxide solution necessary for the formation of disodium 3-amino-1-hydroxypropane-1,1-diphosphonate, for example approximately from 8.5 to 8.7 parts by volume, that is to say approximately 8.6 parts by volume (approximately 11.4 parts by weight) of approximately 30% aqueous sodium hydroxide solution and the whole is heated to approximately 60° C., approximately 50 parts of water are evaporated off at approximately 75° C. until crystallisation begins, approximately from 10 to 15, for example approximately 12.8, parts by volume of ethanol are added and the whole is then cooled to room temperature, stirred for one hour at from approximately 0° to approximately 5° C. to complete the reaction, filtered with suction, washed with approximately 20 parts by volume of approximately 66% ethanol and dried under reduced pressure at approximately 120° C. until the weight is approximately constant.

Because of its excellent storage stability, as already mentioned, the novel crystal modification containing water of crystallisation (modification E) of disodium 3-amino-1-hydroxypropane-1,1-diphosphonate is currently the most suitable solid form of disodium 3-amino-1-hydroxypropane-1,1-diphosphonate for the active ingredient in medicinal preparations intended for enteral, such as oral, but also rectal, administration.

The invention accordingly relates also to the use of this novel crystal modification, containing water of crystallisation, of disodium 3-amino-1-hydroxypropane-1,1-diphosphonate as an active ingredient in, or for the manufacture of, pharmaceutical preparations intended for enteral, preferably oral, administration and pharmaceutical preparations containing the novel crystal modification that contains water of crystallisation (modification E) of disodium 3-amino-1-hydroxypropane-1,1-diphosphonate that are intended for enteral, preferably oral, administration.

The pharmaceutical preparations according to the invention are especially for oral and also rectal administration to warm-blooded animals and contain the pharmacological active ingredient alone or together with a pharmaceutically acceptable carrier. The dosage of the active ingredient depends on the species of warm-blooded animal, age and individual condition and on the method of administration.

In a normal case, the estimated daily dose for a warm-blooded animal weighing approximately 75 kg is, in the case of oral administration, from approximately 0.2 to approximately 200, especially from approximately 1 to approximately 50, mg/kg, advantageously divided into several equal partial doses.

The novel pharmaceutical preparations contain, for example, from approximately 10% to approximately 80%, preferably from approximately 20% to approximately 60%, of active ingredient. Pharmaceutical preparations according to the invention for enteral administration are, for example, those in dosage unit form, such as dragées, tablets, capsules or suppositories. These are manufactured in a manner known per se, for example by means of conventional mixing, granulating, confectioning, dissolving or lyophilising processes. For example, pharmaceutical preparations for oral administration can be obtained by combining the active ingredient with solid carriers, optionally granulating a resulting mixture, and processing the mixture or granulate, if desired or necessary after the addition of suitable adjuncts, to form tablets or dragée cores.

Suitable carriers are, especially, fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores are provided with suitable coatings that may be resistant to gastric juices, there being used, inter alia, concentrated sugar solutions that may contain gum arabic, talc, polyvinylpyrrolidone, polyethylene glycol and/or titanium dioxide, or lacquer solutions in suitable organic solvents or solvent mixtures, or, for the manufacture of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical preparations are dry-filled capsules consisting of gelatine, and also soft sealed capsules consisting of gelatine and a plasticiser, such as glycerine or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may also be added.

There come into consideration as rectally administrable pharmaceutical preparations, for example, suppositories that consist of a combination of the active ingredient and a suppository base. Suitable as suppository bases are, for example, natural or synthetic triglycerides, paraffin hydrocarbons, polyethylene glycols or higher alkanols. It is also possible to use gelatine rectal capsules that contain a combination of the active ingredient and a base material; suitable base materials are, for example, liquid triglycerides, polyethylene glycols or paraffin hydrocarbons.

The following Examples illustrate the invention described above; they are not, however, intended to limit the scope of the invention in any way. Temperatures are given in degrees Celsius, pressures in mbar.

EXAMPLE 1

74.2 g of substantially anhydrous disodium 3-amino-1-hydroxypropane-1,1-diphosphonate are dissolved while stirring in 500 ml of demineralised water in a water bath heated to 75°. The solution is concentrated slowly under reduced pressure until crystallisation begins—this occurs after approximately 375 ml of water have distilled off—and the mixture is allowed to cool slowly to room temperature while stirring. After being left to stand overnight, the mixture is stirred for 1 hour in an ice-bath, filtered with suction, washed with a little ice-cold water and dried under approximately 20 mbar at room temperature until the weight is constant. Disodium 3-amino-1-hydroxypropane-1,1-diphosphonate is thus obtained in the form of the novel crystal modification containing water of crystallisation (modification E). This modification is characterised by the following lattice spacings (d-values) and relative line intensities (intensities) of its X-ray powder pattern (camera according to Guinier-de-Wolff, radiation source: copper-$K_\alpha$):

| d values (Ångstrom) | Intensity |
| --- | --- |
| 10.2 | medium |
| 9.9 | medium |
| 9.2 | very strong |
| 5.91 | very strong |
| 5.57 | strong |
| 5.42 | very weak |
| 5.30 | strong |
| 5.14 | medium |
| 5.02 | very strong |
| 4.97 | very strong |
| 4.63 | very weak |
| 4.41 | strong |
| 4.16 | strong |
| 4.07 | weak |
| 4.04 | medium |
| 3.95 | very weak |
| 3.75 | strong |

-continued

| d values (Ångstrom) | Intensity |
| --- | --- |
| 3.67 | weak |
| 3.63 | medium |
| 3.61 | very weak |
| 3.58 | very weak |
| 3.51 | medium |
| 3.43 | strong |
| 3.38 | medium |
| 3.15 | medium |
| 3.14 | medium |
| 3.09 | medium |
| 3.03 | very strong |
| 3.01 | very strong |
| 2.98 | strong |
| 2.97 | very weak |
| 2.91 | very strong |
| 2.82 | strong |
| 2.80 | medium |
| 2.78 | medium |
| 2.75 | strong |
| 2.73 | weak |
| 2.71 | weak |
| 2.69 | weak |
| 2.67 | medium |
| 2.66 | medium |
| 2.63 | strong |
| 2.62 | strong |
| 2.61 | strong |
| 2.58 | very strong |
| 2.57 | very strong |

The starting material can be manufactured, for example, as follows:

77.1 g of 3-amino-1-hydroxypropane-1,1-diphosphonic acid are suspended in 250 ml of demineralised water, and while stirring vigorously, 65.6 g of 40% aqueous sodium hydroxide solution are added. The rate of addition thereof is so regulated that the temperature of the reaction mixture during neutralisation rises to approximately 50° C. The reaction mixture is heated to 52° C. and inoculated and allowed to cool slowly to room temperature and left to stand overnight; the resulting salt cake is filtered with suction, washed with 120 ml of approximately 66% methanol and dried under 10-20 mbar at 150° C. until the weight is constant. Disodium 3-amino-1-hydroxypropane-1,1-diphosphonate is obtained in a substantially anhydrous crystalline form (modification A). This form is characterised by the following lattice spacings (d-values) and relative line intensities (intensities) of its X-ray powder pattern (camera according to Guinier-de-Wolff, radiation source: copper-$K_\alpha$):

| d-values (Ångstrom) | Intensity |
| --- | --- |
| 11.0 | strong |
| 7.0 | very strong |
| 5.91 | medium |
| 5.69 | very strong |
| 5.63 | very weak |
| 5.52 | medium |
| 5.21 | strong |
| 4.96 | weak |
| 4.84 | very weak |
| 4.73 | medium |
| 4.63 | weak |
| 4.54 | very strong |
| 4.19 | medium |
| 3.90 | strong |
| 3.83 | very weak |
| 3.79 | very weak |
| 3.74 | strong |
| 3.53 | strong |
| 3.47 | medium |
| 3.44 | very strong |

-continued

| d-values (Ångstrom) | Intensity |
| --- | --- |
| 3.35 | medium |
| 3.32 | medium |
| 3.18 | medium |
| 3.14 | very weak |
| 3.09 | very weak |
| 2.98 | weak |
| 2.94 | medium |
| 2.90 | strong |
| 2.85 | strong |
| 2.77 | strong |
| 2.75 | very weak |
| 2.72 | weak |
| 2.68 | weak |
| 2.67 | medium |
| 2.63 | weak |
| 2.61 | strong |
| 2.54 | strong |
| 2.48 | very strong |
| 2.46 | very strong |

EXAMPLE 2

40.0 g of substantially anhydrous disodium 3-amino-1-hydroxypropane-1,1-diphosphonate are suspended in 125 ml of demineralised water and, while stirring vigorously heated until dissolution is complete. The clear solution formed at 59.5° is first cooled to 52° and, once crystallisation has begun, slowly cooled further to room temperature. The mixture is stirred for a further 8 hours at room temperature, filtered with suction, washed with approximately 60 ml of a mixture of 2 parts by volume of methanol and 1 part by volume of water and dried at 28°-31° under approximately 20 mbar until the weight is constant. Disodium 3-amino-1-hydroxypropane-1,1-diphosphonate is obtained in the novel crystal form containing water of crystallisation (modification E), the IR spectrum of which is identical to that of the product obtained according to Example 1.

EXAMPLE 3

70.0 kg of 3-amino-1-hydroxypropane-1,1-diphosphonic acid are suspended while stirring in 140 liters of demineralised water. The suspension is heated to 65°-70° and 59.9 liters (79.5 kg) of 30% aqueous sodium hydroxide solution are added at such a rate that the temperature of the reaction mixture rises to approximately 85° with the formation of a clear solution. The pH value of the solution should be between 7.2 and 7.5. It can be finely adjusted if necessary by the addition of small amounts of 30% sodium hydroxide solution or of 3-amino-1-hydroxypropane-1,1-diphosphonic acid. The solution is cleared by filtering through a filter that is coated with a small quantity of diatomaceous earth and has been preheated to 75°-80° into a vessel preheated to the same temperature. The solution is inoculated, and, while stirring, cooled in the course of 2 hours to 20°-25°, 70 liters of 96% ethanol are added in the course of a further 2 hours while stirring, the mixture is then cooled to 0°-5° in the course of 1 hour and the reaction is completed by stirring at this temperature for at least 1 hour. The mother liquor is then centrifuged off and the residue is washed in portions with a mixture of 25 liters of ethanol and 45 liters of demineralised water. The whole is centrifuged thoroughly and dried in a vacuum cabinet at 35°-40° until the weight is constant (approximately 24 hours). Disodium 3-amino-1-hydroxypropane-1,1-diphosphonate is obtained in the novel crystal form containing water of crystallisation (modification E), the IR spectrum of which is identical to that of the product obtained according to Example 1.

EXAMPLE 4

32.7 g of 3-amino-1-hydroxypropane-1,1-diphosphonic acid are suspended in 106 ml of demineralised water. The suspension is heated to 35° and, while stirring vigorously, 28 ml of 30% aqueous sodium hydroxide solution are added dropwise at such a rate that the temperature of the reaction mixture rises to 54°. A clear solution is obtained initially from which crystallisation begins immediately. The whole is allowed to cool slowly to room temperature while stirring is continued, and then stirred for 8 hours at room temperature, filtered with suction, washed with a mixture of 2 parts by volume of methanol and 1 part by volume of water and dried at 30° under approximately 20 mbar until the weight is constant. Disodium 3-amino-1-hydroxypropane-1,1-diphosphonate is obtained in the novel crystal form containing water of crystallisation (modification E), the IR spectrum of which is identical to that of the product obtained according to Example 1.

EXAMPLE 5

40.0 g of disodium 3-amino-1-hydroxypropane-1,1-diphosphonate in the crystal form of modification C which contains relatively little water, are suspended in 100 ml of demineralised water and stirred at room temperature overnight. The crystals are left to stand for a few more hours in the mother liquor in an ice-bath, filtered with suction, washed with a little ice-water and dried at room temperature under reduced pressure (approximately 20 mbar) until the weight is constant. Disodium 3-amino-1-hydroxypropane-1,1-diphosphonate is obtained in the novel crystal form containing water of crystallisation (modification E), the IR spectrum of which is identical to that of the product obtained according to Example 1.

235 g of 3-amino-1-hydroxypropane-1,1-diphosphonic acid are suspended in 2.17 liters of demineralised water and, while stirring, heated to 60° C. 30% aqueous sodium hydroxide solution is then added until the pH value is 7.5, for which purpose approximately 200 ml are required. The whole is heated to 70°, approximately 1.2 liters of water are distilled off under reduced pressure until crystallisation begins and 300 ml of ethanol are added while stirring. The whole is then cooled to room temperature while stirring, and the reaction is completed by stirring for 1 hour in an ice-bath, filtered with suction, washed with 400 ml of 66% ethanol and dried under reduced pressure (approximately 20 mbar) at 120° until the weight is constant. The crystalline modification C, which contains less water than the crystal modification containing water of crystallisation according to the invention (modification E), of disodium 3-amino-1-hydroxypropane-1,1-diphosphonate is obtained. This modication is characterised by the following lattice spacings (d-values) and relative line intensities (intensities) of its X-ray powder pattern (camera according to Guinier-de-Wolff, radiation source: copper-$K_\alpha$):

| d-values (Ångstrom) | Intensity |
| --- | --- |
| 10.1 | very weak |
| 9.1 | medium |
| 8.9 | weak |
| 6.6 | very weak |
| 5.91 | weak |
| 5.67 | very weak |
| 5.49 | strong |
| 4.90 | strong |
| 4.73 | medium |
| 4.54 | medium |
| 4.19 | weak |
| 3.61 | very weak |
| 3.13 | weak |
| 3.11 | weak |
| 3.06 | weak |
| 3.03 | very weak |
| 2.98 | weak |
| 2.91 | weak |
| 2.86 | medium |

EXAMPLE 6

10 kg of crude disodium 3-amino-1-hydroxy-1,1-diphosphonate having a water content of approximately 7.3% by weight (determined by removing by heating at approximately 180°) are spread on drying sheets and introduced into a circulating-air cabinet dryer, the other sheets of which are filled with water. The dryer is operated on the circulating-air principle at the lowest fan power setting until the substance has increased in weight by approximately from 23 to 26%. The water-filled sheets are then removed and drying is effected at approximately 35° using the mixed-air setting until the weight is constant. Disodium 3-amino-1-hydroxypropane-1,1-diphosphonate is obtained in the novel crystal form containing water of crystallisation (modification E), the IR spectrum of which is identical to that of the product obtained according to Example 1.

COMPARISON EXAMPLE 1

2.35 g of 3-amino-1-hydroxypropane-1,1-diphosphonic acid are suspended in 100 ml of water and, while stirring, 1N sodium hydroxide solution (approximately 20.0 ml) is added dropwise until neutralisation is complete (pH=7.4). The whole is concentrated to dryness by evaporation under reduced pressure at 60°–70° and dried under reduced pressure (approximately 20 mbar) until the weight is constant. Disodium 3-amino-1-hydroxypropane-1,1-diphosphonate is obtained in the form of an amorphous product that is deliquescent in air and that according to Karl Fischer titration contains approximately 12.9% by weight of water.

COMPARISON EXAMPLE 2

50.0 g of 3-amino-1-hydroxypropane-1,1-diphosphonic acid are suspended in 370 ml of demineralised water and, while stirring, heated to 50°. 56.6 g of 30% aqueous sodium hydroxide solution are then added in such a manner that the temperature of the reaction mixture during neutralisation rises to 59°. The reaction mixture is heated to 65°, filtered hot over diatomaceous earth, heated to 75° and, while stirring, 300 ml of water are distilled off under reduced pressure. The mixture is allowed to cool to approximately 52°, and inoculated and allowed to cool slowly to room temperature while stirring, crystallisation starting at approximately 45°. The crystals are left to stand in the mother liquor overnight, stirred for 1 hour in an ice bath to complete the reaction, filtered with suction, washed with a little ice-water and dried under reduced pressure at room temperature until the weight is constant. Disodium 3- amino-1-hydroxypropane-1,1-diphosphonate is obtained in the granular-crystalline crystal form of modification B which contains less water than the crystal modification containing water of crystallisation according to the invention (modification E). This form is characterised by the following lattice spacings (d-values) and relative line intensities (intensities) of its X-ray powder pattern (camera according to Guinier-de-Wolff, radiation source: copper-$K_\alpha$):

| d-values (Ångstrom) | Intensity |
| --- | --- |
| 11.7 | strong |
| 7.8 | very strong |
| 6.8 | very strong |
| 5.83 | strong |
| 5.66 | strong |
| 5.38 | very weak |
| 4.76 | medium |
| 4.66 | medium |
| 4.29 | very weak |
| 4.20 | very weak |
| 4.13 | weak |
| 4.06 | medium |
| 3.99 | medium |
| 3.89 | medium |
| 3.82 | strong |
| 3.76 | very weak |
| 3.63 | medium |
| 3.51 | weak |
| 3.46 | strong |
| 3.27 | weak |
| 3.22 | very weak |
| 3.15 | strong |
| 3.08 | strong |
| 3.01 | weak |
| 2.94 | weak |
| 2.91 | strong |
| 2.89 | strong |
| 2.86 | weak |
| 2.82 | strong |
| 2.78 | medium |

The X-ray powder pattern is different from those of modifications A, C and E.

COMPARISON EXAMPLE 3

The process of Comparison Example 2 is followed, with the difference that, in order to dry the crude product, it is heated under reduced pressure at 120° until the weight is constant. Disodium 3-amino-1-hydroxypropane-1,1-diphosphonate is obtained in a substantially anhydrous crystalline form (modification A). According to the IR spectrum the product is identical to the starting material of Example 1.

FORMULATION EXAMPLE 1

Gelatine capsules containing 200 mg of the novel crystal modification, containing water of crystallisation, of disodium 3-amino-1-hydroxypropane-1,1-diphosphonate (modification E) as active ingredient can be manufactured, for example, as follows:

| Composition (for 1000 capsules) | |
| --- | --- |
| active ingredient | 100 g |
| lactose, ground | 100 g |

The active ingredient and the lactose (very finely ground) are mixed together well. The resulting powder is sieved and introduced into gelatine capsules in portions of 0.20 g.

FORMULATION EXAMPLE 2

Tablets containing 25 mg of the novel crystal modification, containing water of crystallisation, of disodium 3-amino-1-hydroxypropane-1,1-diphosphonate (modification E) can be obtained as follows:

| Constituents (for 1000 tablets) | |
| --- | --- |
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture

All the solid ingredients are first forced through a sieve of 0.6 mm mesh width. Then the active ingredient, the lactose, the talc, the magnesium stearate and half the starch are mixed. The other half of the starch is suspended in 40 ml of water and this suspension is added to a boiling solution of the polyethylene glycol in 100 ml of water and the mixture, if necessary with the addition of water, is granulated. The granulate is dried overnight at 35°, forced through a sieve of 1.2 mm mesh width and compressed to form tablets having a diameter of approximately 6 mm that are concave on both sides.

FORMULATION EXAMPLE 3

Tablets containing 100 mg of the novel crystal modification, containing water of crystallisation, of disodium 3-amino-1-hydroxypropane-1,1-diphosphonate (modification E) can be manufactured as follows:

| Constituents (for 1000 tablets) | |
| --- | --- |
| active ingredient | 100.0 g |
| lactose | 50.7 g |
| wheat starch | 7.5 g |
| polyethylene glycol 6000 | 5.0 g |
| talc | 5.0 g |
| magnesium stearate | 1.8 g |
| demineralised water | q.s. |

MANUFACTURE

All the solid ingredients are first forced through a sieve of 0.6 mm mesh width. Then the active ingredient, the lactose, the talc, the magnesium stearate and half the starch are mixed. The other half of the starch is suspended in 40 ml of water and this suspension is added to a boiling solution of the polyethylene glycol in 100 ml of water and the mixture, if necessary with the addition of water, is granulated. The granulate is dried overnight at 35°, forced through a sieve of 1.2 mm mesh width and compressed to form tablets having a diameter of approximately 6 mm that are concave on both sides.

FORMULATION EXAMPLE 4

Tablets containing 75 mg of the novel crystal modification, containing water of crystallisation, of disodium 3-amino-1-hydroxypropane-1,1-diphosphonate (modification E) as active ingredient can be manufactured as follows:

| Constituents (for 1000 tablets) | |
|---|---|
| active ingredient | 75.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Manufacture

All the solid ingredients are first forced through a sieve of 0.6 mm mesh width. Then the active ingredient, the lactose, the talc, the magnesium stearate and half the starch are mixed. The other half of the starch is suspended in 40 ml of water and this suspension is added to a boiling solution of the polyethylene glycol in 100 ml of water and the mixture, if necessary with the addition of water, is granulated. The granulate is dried overnight at 35°, forced through a sieve of 1.2 mm mesh width and compressed to form tablets having a diameter of approximately 6 mm that are concave on both sides.

We claim:

1. Process for the manufacture of disodium 3-amino-1-hydroxypropane-1,1-diphosphonate in a crystalline form that contains water of crystallisation, characterised in that disodium 3-amino-1-hydroxypropane-1,1-diphosphonate is caused to crystallise from a water-containing solution or that a solid form of disodium 3-amino-1-hydroxypropane-1,1-diphosphonate containing relatively little water is treated with water, and in each case the product is isolated and dried at normal or slightly elevated temperature.

2. Process according to claim 1, characterised in that an approximately 10% to approximately 55% aqueous solution of disodium 3-amino-1-hydroxypropane-1,1-diphosphonate is concentrated at from approximately 70° C. to approximately 80° C. to the saturation concentration of disodium 3-amino-1-hydroxypropane-1,1-diphosphonate and crystallisation is effected by cooling slowly to approximately from 0° C. to 5° C., or in that an approximately 35% to approximately 45% aqueous solution of disodium 3-amino-1-hydroxypropane-1,1-diphosphonate is cooled from an initial temperature of from approximately 70° C. to approximately 80° C. until the start of crystal formation, but to not less than 55° C., and crystallisation is effected by cooling slowly to from approximately 20° C. to approximately 25° C., adding approximately from 35 to 45% by volume (based on the total amount of water) of ethanol and cooling slowly to from approximately 0° C. to 5° C.

3. Process according to claim 1, characterised in that a crystalline form of disodium 3-amino-1-hydroxypropane-1,1-diphosphonate that contains relatively little water is treated with at least that amount of water that is required for the formation of the novel crystal modification containing water of crystallisation and at most that amount of water that corresponds to the reciprocal value, reduced by 1, of the saturation concentration of disodium 3-amino-1-hydroxypropane-1,1-diphosphonate.

4. Process according to claim 3 characterised in that stirring is carried out with approximately from 2 to 3 times the amount by weight of water.

5. Process according to claim 1, characterised in that drying is carried out at from approximately 18° C. to approximately 25° C. or at from approximately 35° C. to approximately 40° C.

6. Process according to claim 1, characterised in that drying is effected under reduced pressure.

7. Process according to claim 1, characterised in that moist air having a relative humidity of from approximately 90% to approximately 99% is allowed to act on a crystalline form of disodium 3-amino-1-hydroxypropane-1,1-diphosphonate that contains relatively little water, at from approximately 20° C. to approximately 25°0 C., until there is a weight increase of at least approximately 32.2% by weight (taking into consideration the initial water content), and the atmospheric humidity is then gradually reduced to from approximately 35% to approximately 80%.

8. Process according to claim 1, characterised in that as the solid form of disodium 3-amino-1-hydroxypropane-1,1-diphosphonate that contains relatively little water there is used substantially anhydrous disodium 3-amino-1-hydroxypropane-1,1-diphosphonate.

9. Process according to claim 1, characterised in that as the solid form of disodium 3-amino-1-hydroxypropane-1,1-diphosphonate that contains relatively little water there is used disodium 3-amino-1-hydroxypropane-1,1-diphosphonate having a water content of approximately 5 to 10% by weight, determined by removing by heating at approximately 180° C.

10. Process for the manufacture of disodium 3-amino-1-hydroxypropane-1,1-diphosphonate in a crystalline form that contains water of crystallisation by reacting 3-amino-1-hydroxypropane-1,1-diphosphonic acid with a basic sodium salt suitable for the partial neutralisation thereof, characterised in that 3-amino-1-Hydroxypropane-1,1-diphosphonic acid in a water-containing suspension and/or solution is reacted with the requisite amount of aqueous sodium hydroxide solution, the resulting disodium 3-amino-1-hydroxypropane-1,1-diphosphonate is caused to crystallise from an at least saturated water-containing solution in the form of the novel form containing water of crystallisation, and the product is isolated and dried at normal or slightly elevated temperature, wherein the reaction conditions are so selected that neutralisation takes place at from approximately 35° C. to approximately 85° C., initial crystal formation takes place at at least 50° C. and crystal growth takes place predominantly at from approximately 50° C. to approximately 0° C.

11. Process according to claim 10, characterised in that a suspension of 10 parts by weight of 3-amino-1-hydroxypropane-1,1-diphosphonic acid in approximately from 18 to 23 parts by volume of water is neutralised at from approximately 65° C. to approximately 85° C. with that amount of approximately 30% aqueous sodium hydroxide solution that is required for the formation of disodium 3-amino-1-hydroxypropane-1,1-diphosphonate, that is to say approximately from 8.5 to 8.7, parts by volume, the resulting solution is allowed to cool to from approximately 70° C. to approximately 55° C. and, when crystal formation has begun or been initiated, then cooled slowly to approximately from 20° C. to 25° C., approximately from 7 to 12 parts by volume of ethanol are added and the whole is cooled slowly to approximately from 5° C. to 0° C. and stirred at this temperature for approximately from 1 to 15 hours, and the product is isolated by filtering with suction or centrifuging, washed in portions with a total of approximately 7.5 to 12.5 parts by volume of approximately 40 to 60% aqueous ethanol or that a suspension of 10 parts by weight of 3-amino-1-hydroxypropane-1,1-diphosphonic acid in approximately from 25 to 37.5 parts by volume of water is neutralised at an initial temperature of approximately 35° C. with that amount of approximately 30% aqueous sodium hydroxide solution that is required for the formation of disodium 3-amino-1-hydroxypropane-1,1-diphosphonate, that is to say approximately from 8.5 to 8.7 parts by volume, the rate of addition thereof being so adjusted that the temperature rises to approximately from 50° C. to 55° C. and, when crystallisation has begun or been initiated, the whole is allowed to cool slowly to from approximately 18° C. to approximately 25° C., and the product is isolated by filtering with suction, washed in portions with a total of approximately from 15 to 25 parts by volume of from approximately 50 to 75% aqueous ethanol, and in either case subsequently dried under from approximately 5 to approximately 25 mbar at from approximately 35° C. to approximately 40° C. until the weight is constant.

* * * * *